US00PP07951P

United States Patent [19]

Warriner

[11] Patent Number: Plant 7,951

[45] Date of Patent: Aug. 25, 1992

[54] ROSE PLANT JACLING

[75] Inventor: William A. Warriner, Tustin, Calif.

[73] Assignee: Bear Creek Gardens, Inc., Medford, Oreg.

[21] Appl. No.: 625,913

[22] Filed: Dec. 10, 1990

[51] Int. Cl.[5] ..... A01H 5/00

[52] U.S. Cl. ..... Plt./26

[58] Field of Search ..... Plt./22, 25, 26

*Primary Examiner*—Howard J. Locker

*Attorney, Agent, or Firm*—Klarquist, Sparkman, Campbell, Leigh and Whinston

[57] ABSTRACT

A floribunda class rose plant having continuous, heavy production of light pink, moderately scented flowers, a compact spreading habit of growth, resistance to powdery mildew and rose rust and a high level of tolerance to blackspot.

1 Drawing Sheet

The present invention relates to a new and distinct variety of rose plant of the floribunda class which was originated by me by crossing the variety Jacjem, U.S. Plant Pat. No. 5,001, with the variety Jacink, U.S. Plant Pat. No. 4,089.

The primary objective of this breeding was to produce a new rose variety having the quite dwarf spreading habit of Jacjem but with the continuous bloom of Jacink. The objective was substantially achieved along with other desirable improvements as evidenced by the following unique combination of characteristics which are outstanding in the new variety and which distinguish it from its parents, as well as from all other varieties of which I am aware:

1. Continuous, heavy production of light pink, moderately scented flowers.
2. A compact spreading habit of growth.
3. Resistance to powdery mildew and rose rust and a high level of tolerance to blackspot.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with the Royal Horticultural Society (London) Colour Chart, except where ordinary dictionary significance of color is indicated.

Parentage:

*Seed parent.*—Jacjem, U.S. Plant Pat. No. 5,001.

*Pollen parent.*—Jacink, U.S. Plant Pat. No. 4,089.

Classification:

*Botanical.*—Rosa hybrida.

*Commercial.*—Floribunda.

FLOWER

Observations made from specimens grown in a garden in Somis, Calif., in September, 1990.

Blooming habit: Continuous.

Bud:

*Size.*—1¼ inches when the petals start to unfurl.

*Form.*—Long, pointed ovoid.

*Color.*—When sepals first divide, bud color is Red Group 36C, with the pink color changing to Yellow green 154D at the petal base. When half blown, the upper sides of the petals are Red Group 36C; and the lower sides of the petals are Red Group 36C.

*Sepals.*—Color: Green Group 138C. Surface texture: Covered with fine hairs. There are three normally appendaged sepals. There are two unappendaged sepals with hairy edges.

*Receptacle.*—Color: Green 138B. Shape: Funnel. Size: Medium (¼"×¼"). Surface: Smooth.

*Peduncle.*—Length: Short (2 to 2½"). Surface: Glandular. Color: Light Green. Strength: Stiff, erect, slender.

Bloom:

*Size.*—Medium. Average open size is 4 inches.

*Borne.*—Several together, in slightly pyramidal to flat clusters.

*Stems.*—Short (10 to 12").

*Form.*—When first open: High center. Permanence: Flattens, outer petals curl back.

*Petalage.*—Number of petals under normal conditions: 20 to 25.

*Color.*—The upper side of the petals is Red Group 36C. The reverse side of the petals is Red Group 36C. The base of the petals have Yellow-green half moons 154D. The major color on the upper side is Red Group 36C.

*Variegations.*—None.

*Discoloration.*—No change in the general tonality at the end of the first day: No change in tonality at the end of the third day.

*Fragrance.*—Moderate.

Petals:

*Texture.*—Thick, leathery.

*Shape.*—Deltoid.

*Form.*—Tips slightly recurved.

*Arrangement.*—Imbricated. Petaloids in the center: Very few.

*Persistence.*—Drop off cleanly.

*Lastingness.*—On the plant: Short (3 to 4 days). As a cut flower: Short (3 to 4 days).

Reproductive parts:

*Anthers.*—Size: Medium. Quantity: Many. Color: Yellow. Arrangement: Regular around styles.

*Filaments.*—Color: Yellow.

*Pollen.*—Color: Lemon yellow.

*Styles.*—Color: Red.

*Stigmas.*—Color: Greenish white.

Form: Bush.

Growth: Vigorous, upright, branching, compact, spreading.

Foliage: Number of leaflets on normal mid-stem leaves: 5 or 7.

*Size.*—Large (6½"×4½").

*Quantity.*—Abundant.

*Color.*—New foliage: Reddish. Old foliage: Medium green matte finish.

Leaflets:

*Shape.*—Pointed oval.

*Texture.*—Upper side: Smooth.

*Edge.*—Serrated.

*Serration.*—Single, small.

*Petiole rachis.*—Color: Green.

*Petiole underside.*—Rough, with prickles and glands.

*Stipules.*—Medium (½"), bearded.

*Disease resistance.*—Resistant to mildew and rust under normal growing conditions at Somis, Calif. Also quite tolerant to blackspot.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Medium straight to hooked slightly downward.

*Color when young.*—Red.

Small Prickles:

*Quantity.*—On main stalks: Few. On laterals: Few.

I claim:

1. A new and distinct variety of rose plant of the floribunda class, substantially as herein shown and described, characterized particularly as to novelty by the unique combination of its heavy bloom production, continuous bloom production, unique very light pink color, good level of disease resistance, compact spreading habit and moderate scent.

* * * * *

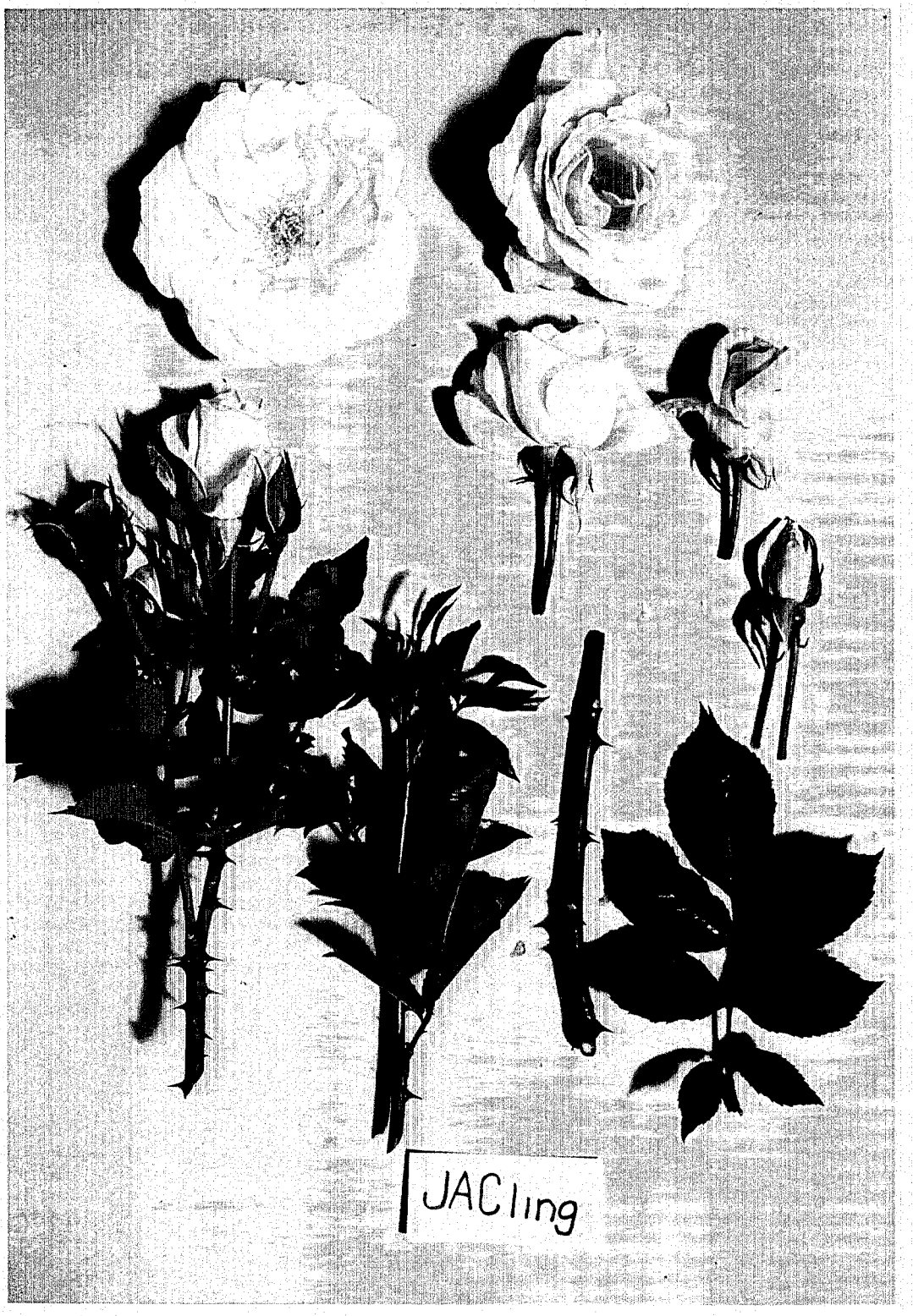
JACling